United States Patent
Iwata et al.

(10) Patent No.: US 10,238,714 B2
(45) Date of Patent: Mar. 26, 2019

(54) METHOD FOR FORMING AN IMMUNE-TOLERANT SITE AND METHOD FOR ATTRACTING IMMUNOSUPPRESSIVE CELLS

(71) Applicants: KYOTO UNIVERSITY, Kyoto-shi, Kyoto (JP); ARKRAY, Inc., Kyoto-shi, Kyoto (JP); KYOTO PREFECTURAL PUBLIC UNIVERSITY CORPORATION, Kyoto-shi, Kyoto (JP)

(72) Inventors: Hiroo Iwata, Kyoto (JP); Rei Kuwabara, Kyoto (JP); Masahide Hamaguchi, Kyoto (JP); Kunio Hirano, Kyoto (JP); Shimon Sakaguchi, Kyoto (JP)

(73) Assignees: KYOTO UNIVERSITY, Kyoto (JP); ARKRAY, Inc., Kyoto (JP); KYOTO PREFECTURAL PUBLIC UNIVERSITY CORPORATION, Kyoto (JP)

(*) Notice: Subject to any disclaimer, the term of this patent is extended or adjusted under 35 U.S.C. 154(b) by 380 days.

(21) Appl. No.: 15/097,390

(22) Filed: Apr. 13, 2016

(65) Prior Publication Data

US 2016/0303188 A1  Oct. 20, 2016

(30) Foreign Application Priority Data

Apr. 14, 2015  (JP) ................. 2015-082847

(51) Int. Cl.
| | | |
|---|---|---|
| A61K 38/15 | (2006.01) | |
| A61K 38/12 | (2006.01) | |
| A61K 38/18 | (2006.01) | |
| A61K 9/00 | (2006.01) | |

(52) U.S. Cl.
CPC ............ *A61K 38/15* (2013.01); *A61K 9/0024* (2013.01); *A61K 38/12* (2013.01); *A61K 38/1825* (2013.01)

(58) Field of Classification Search
None
See application file for complete search history.

(56) References Cited

U.S. PATENT DOCUMENTS

| | | |
|---|---|---|
| 5,858,971 A | 1/1999 | Fujiwara et al. |
| 2003/0091541 A1 | 5/2003 | Ikehara et al. |
| 2003/0232057 A1 | 12/2003 | Turini et al. |
| 2010/0272697 A1 | 10/2010 | Naji et al. |
| 2010/0303909 A1 | 12/2010 | Oh et al. |
| 2011/0070645 A1 | 3/2011 | Chen et al. |
| 2016/0120932 A1 | 5/2016 | Iwata et al. |
| 2016/0228473 A1 | 8/2016 | Iwata et al. |

FOREIGN PATENT DOCUMENTS

| | | |
|---|---|---|
| EP | 0494664 A1 | 7/1992 |
| EP | 3015113 A1 | 5/2016 |
| JP | H0665088 A | 3/1994 |
| JP | H10120591 A | 5/1998 |
| JP | H10-259134 A | 9/1998 |
| JP | 2000-178180 A | 6/2000 |
| JP | 3089299 B2 | 9/2000 |
| JP | 2001-172188 A | 6/2001 |
| JP | 2001-299908 A | 10/2001 |
| JP | 3673304 B2 | 7/2005 |
| JP | 2008-260692 A | 10/2008 |
| WO | 96/12732 A1 | 5/1996 |
| WO | 2005/072764 A2 | 8/2005 |
| WO | 2015/041357 A1 | 3/2015 |

OTHER PUBLICATIONS

Gu, Yuanjun, et al. "Development of a new method to induce angiogenesis at subcutaneous site of streptozotocin-induced diabetic rats for islet transplantation." Cell transplantation 10.4-5 (2001): 453-457. (Year: 2001).*
Cai, Shenshen, et al. "Injectable glycosaminoglycan hydrogels for controlled release of human basic fibroblast growth factor." Biomaterials 26.30 (2005): 6054-6067 (Year: 2005).*
International Search Report issued in PCT/JP2014/074973 dated Dec. 16, 2014.
International Preliminary Report on Patentability issued in PCT/JP2014/074973 dated Mar. 24, 2016.
Kazutomo Inoue, "A Study on the Rejection Mechanism in Islet Transplantation and the Avoidance thereof", Research report from "Research on the Human Genome, Tissue Engineering, and Food Biotechnology", via a FY 2000 grant for health sciences, Mar. 2001, pp. 37-43.
Abe Y et al., "Wound healing acceleration of a novel transforming growth factor-b inducer, SEK-1005" European Journal of Pharmacology, Elsevier Science, vol. 408, No. 2, Jan. 1, 2000, pp. 213-218.
Sano Hiroki et al., "Coils Coated With the Cyclic Peptide SEK-1005 Accelerate Intra-Aneurysmal Organization", Official Journal of the Congress of Neurological Surgeons, Neurosurgery, vol. 67, No. 4, Oct. 1, 2010, pp. 984-992.
Luan N. M. et al., "Long-Term Allogeneic Islet Graft Survival in Prevascularized Subcutaneous Sites Without Immunosuppressive Treatment", American Journal of Transplantation, vol. 14, No. 7, Jul. 6, 2014, pp. 1533-1542.

(Continued)

*Primary Examiner* — Robert J Yamasaki
(74) *Attorney, Agent, or Firm* — Studebaker & Brackett PC (57) ABSTRACT

A method for forming an immune-tolerant site, and a method for attracting immunosuppressive cells, comprising contacting an agent comprising SEK-1005 (Ser, 3-hydroxy-N-[2-hydroxy-1-oxo-2-tetrahydro-2-hydroxy-6-methyl-5-(2-methylpropyl)-2H-pyran-2-yl-propyl]-Leu-Pip(hexahydro-3-pyridazinecarbonyl)-N-hydroxy-Ala-N-methyl-Phe-Pip-rho-lactone) and/or fibroblast growth factor (FGF) with a site in the body tissue.

8 Claims, 5 Drawing Sheets

(56) References Cited

OTHER PUBLICATIONS

Extended European Search Report (EESR) dated Feb. 23, 2016 issued in European Application No. 15192456.0.

Kobayashi et al., "Indefinite Islet Protection From Autoimmune Destruction in Nonobese Diabetic Mice by Agarose Microencapsulation Without Immunosuppression", Transplantation, vol. 75, No. 5, 2003, pp. 619-625.

Kuriyama et al., "Anti-inflammatory action of a novel peptide, SEK-1005, isolated from a Streptomyces", European Journal of Pharmacology, vol. 390, 2000, pp. 223-228.

Koh et al., "In Vitro Three Dimensional Collagen Matrix Models of Endothelial Lumen Formation During Vasculogenesis and Angiogenesis", Methods in Enzymology, vol. 443, 2008, pp. 83-101.

Cheng et al., "Inhibition of dendritic cell differentiation and accumulation of myeloid-derived suppressor cells in cancer is regulated by S100A9 protein", Journal of Experimental Medicine, vol. 205, No. 10, 2008, pp. 2235-2249.

Sakai et al.; "Promotion of vascular endothelial cell migration and tube formation by SEK-1005"; Journal of Pharmacological Sciences; Mar. 19, 2014; 224P; Abstract No. P3-8-8; vol. 124 (Supplement 1); Sendai, Japan.

An Office Action issued by the U.S. Patent Office dated Dec. 1, 2017, which is related to U.S. Appl. No. 14/928,049 and is related to U.S. Appl. No. 15/097,390.

Extended European Search Report issued in the corresponding European Patent Application No. 14845238.6 dated Feb. 15, 2017.

Kawakami et al., "Successful Subcutaneous Pancreatic Islet Transplantation Using an Angiogenic Growth Factor-Releasing Device", Pancreas, vol. 23, No. 4, pp. 375-381, 2001.

Communication pursuant to Article 94(3) EPC issued by the European Patent Office dated May 7, 2018, which corresponds to European Patent Application No. 16 165 037.9-1112, and related to U.S. Appl. Nos. 14/928,049 and 15/097,390.

U.S. Appl. No. 14/928,049, filed Oct. 30, 2015, Transplant Site-Forming Agent, Transplant Site-Forming Device, Angiogenic Agent and Angiogenic Device.

U.S. Appl. No. 15/022,781, filed Mar. 17, 2016, Device and Method for Immunosuppressant-Free Transplantation, and Usage Thereof.

Ludwig et al., Improvement of islet function in a bioartificial pancreas by enhanced oxygen supply and growth hormone releasing hormone agonist, PNAS Mar. 27, 2012, vol. 109, No. 13.

Vaithilingam et al., Islet Transplantation and Encapsulation: An Update on Recent Developments, The Review of Diabetic Studies, vol. 8, No. 1, 2011.

Shapiro et al., Islet Transplantation in Seven Patients With Type 1 Diabetes Mellitus Using a Glucocorticoid-free Immunosuppressive Regimen, The New England Journal of Medicine, vol. 343, No. 4, Jul. 27, 2000.

An Office Action mailed by the Japanese Patent Office dated Aug. 7, 2018, which corresponds to Japanese Patent Application No. 2015-082847 and is related to U.S. Appl. No. 15/097,390; with English Translation.

Rei Kuwabara et al., "Regenerative Medicine", 2015, p. 249, O-43-5, vol. 14, Supplemental Issue.

Extended European Search Report dated Sep. 1, 2016 issued in European Application No. 16165037.9 corresponding to the related U.S. Appl. No. 15/097,390.

Kuwabara Rei et al., "Preparation of immune tolerance site by cyclic peptide for islets transplantation at subcutaneous sites", Xenotransplantation, Wiley-Blackwell Publishing, Inc., US, vol. 22, No. Suppl.1, Nov. 2015, pp. S104-S105.

Database WPI Week 200220 Thomson Scientific, London, GB; AN2002-151143.

Database WPI Week 200260 Thomson Scientific, London, GB; AN 2002-561192 and JP 2002 145797 A (Kaken Pharm Co Ltd) May 22, 2002.

Database WPI Week 200326 Thomson Scientific, London, GB; AN 2003-268161 and WO 03/013588 A1 (Kaken Pharm Co Ltd) Feb. 20, 2003.

* cited by examiner

METHOD FOR FORMING AN IMMUNE-TOLERANT SITE AND METHOD FOR ATTRACTING IMMUNOSUPPRESSIVE CELLS

TECHNICAL FIELD

The present invention relates to a method for forming an immune-tolerant site and a method for attracting immunosuppressive cells.

BACKGROUND ART

For treatment of diseases due to failure of biological functions, such as diabetes, transplantation of an organ/tissue is an effective therapeutic method. However, in cases of allotransplantation, which causes immune rejection, and in cases of diseases that occur due to autoimmunity such as type I diabetes, patients need to regularly take an immunosuppressant after the transplantation. Since, in general, immunosuppressants nonspecifically suppress immune function, they are known to increase the risk of infections and cancer development, and to cause hypertension, hyperglycemia, and disorders of the liver and kidney as side effects.

On the other hand, a state called immune tolerance is known. Immune tolerance means suppression of action of the immune system against a particular substance. Immune tolerance is a system which allows the immune system to recognize autologous substances as the self, and regulates the immune system such that it does not attack those substances. It is also known that immune tolerance also occurs for nonself such as orally ingested substances such as foods, so that an excessive immune response can be avoided. Some cancers have been shown to be capable of acquiring immune tolerance to avoid attack by the immune system.

Although the mechanism of immune tolerance has not been fully clarified, processes such as central tolerance (disappearance of immune cells reactive with the self) and peripheral tolerance (suppression of, or loss of responsiveness of, reactive immune cells) are known. Examples of cell species which induce peripheral tolerance in the body include regulatory T cells (Tregs) and myeloid-derived suppressor cells (MDSCs). It is thought that, if a method for achieving immune tolerance to a transplanted organ/tissue upon transplantation of the organ/tissue can be established, the need to administer an immunosuppressant can be eliminated.

As a device for formation of a capillary-rich site suitable for tissue transplantation, JP 3089299 B discloses a device using a hydrogel (e.g., agarose) as a substrate. This document mentions growth factors (bFGF, aFGF, PDGF, VEGF, TGF-β, and the like) as factors that induce angiogenesis. However, since the device was developed for the purpose of supplying nutrition and oxygen, there is no discussion on immune tolerance in the document.

American Journal of Transplantation 2014, 14: 1533-1542 describes results of a study in which pancreatic islets were transplanted to a space formed under the skin of a rat using the device described in JP 3089299 (using bFGF+heparin as inducers). The document reports that the transplanted tissue could be maintained for a long period without occurrence of rejection irrespective of the fact that the transplantation was allotransplantation and no immunosuppressant was administered. However, its mechanism has not been studied.

JP 10-306027 A discloses a method in which immune tolerance is induced by intraportal or intravenous administration of a tolerogen containing a hematopoietic stem cell, hemopoietic progenitor cell, and/or mature lymphocyte. However, this technique requires cell transplantation, and the cells to be transplanted need to be obtained from bone marrow or the like.

JP 2001-172188 A discloses a method in which a tolerogen containing bone marrow cells is irradiated with radiation, and then administered into bone marrow to induce immune tolerance. However, this technique requires cell transplantation, and the cells to be transplanted need to be obtained from bone marrow or the like.

JP 6-65088 A discloses an immune tolerance inducer comprising, as active ingredients, a cytotoxic cytokine (a physiologically active substance having cytotoxic activity against immune cells, such as lymphotoxin), and an allergic antigen, autoantigen, or transplanted-organ antigen. However, this technique requires administration of the antigen and the cytotoxic factor. Further, since this inducer is effective only for the particular antigen, the factor to which immune tolerance is to be induced needs to be specified.

JP 10-120591 discloses a method for preparing an antigen-specific immune tolerance inducer by binding a peptide composed of 5 to 25 amino acids containing a B-cell epitope and/or T-cell epitope of the B subunit constituting an AB toxin (e.g., cholera toxin or enterotoxin) to the antigen to which immune tolerance is to be induced, via an appropriate spacer. However, this technique requires design/preparation/administration of an agent specific to the antigen. Moreover, since this inducer is effective only for the particular antigen, the factor to which immune tolerance is to be induced needs to be specified.

JP 2004-522725 discloses a method for inducing tolerance to an antigenic substance by administering, to an individual, the antigenic substance or an antigenic portion thereof together with at least one substance which increases the intracellular COX-2 activity and/or the IFN-γ level in the individual. However, this technique requires design/preparation/administration of an agent specific to the antigen. Moreover, since this method is effective only for the particular antigen, the factor to which immune tolerance is to be induced needs to be specified.

SUMMARY OF THE INVENTION

Conventionally, transplantation of islets of Langerhans (pancreatic islets) for treatment of diabetes, and transplantation of cells secreting hormones and proteins for complementing deficiency of those hormones and proteins, have often been attempted not only in studies using animals, but also at clinical sites. However, because of a limited number of donors who donate the cells and tissues, it has been difficult to treat all patients awaiting such therapeutic methods.

In recent years, methods of inducing differentiation of various stem cells such as embryonic stem cells (ES cells) and induced pluripotent stem cells (iPS cells) into various functional cells have begun to be established. Establishment of the differentiation induction methods will provide an unlimited supply of secretory cells, and make cell transplantation therapies available to all patients awaiting the therapies.

However, cell transplantation has common problems such as rejection caused by the immune system of the recipient, and the site of transplantation.

Normally, an immunosuppressant is administered to control rejection. However, administration of an immunosuppressant has problems such as susceptibility to infection and an increased risk of development of a malignant tumor. Moreover, administration of an immunosuppressant requires a relatively high health care cost such as 1.5 million yen/year.

Therefore, an object of the present invention is to provide a useful agent which is capable of efficiently inducing immune tolerance in, or at, a specific site, which agent eliminates, upon transplantation of cells to the site, the need for administration of an immunosuppressant, a therapeutic agent for an autoimmune disease, or the like which has previously been required in transplantation.

Transplantation of cells, a tissue, or an organ prepared by differentiation induction of iPS cells derived from another individual or from the patient himself is expected to enable transplantation without causing rejection or an autoimmune response. However, since type I diabetes, to which pancreatic islet transplantation is applied, occurs due to an autoimmune response to autologous cells, the transplanted cells are killed by the autoimmune response after transplantation of β-cells or pancreatic islets derived from the patient himself, as reported in Transplantation. 2003, Mar. 15; 75(5): 619-25. As shown in this example, in diseases that occur due to an autoimmune response, treatment for suppression of a certain immune response is necessary even in cases of transplantation of cells, a tissue, or an organ prepared by differentiation induction of iPS cells derived from the patient himself.

In order to solve the problem described above, the present invention provides an agent for forming an immune-tolerant site comprising SEK-1005 and/or fibroblast growth factor (FGF). The present invention also provides an agent for attracting immunosuppressive-cells such as regulatory T cells (Tregs) and/or myeloid-derived suppressor cells (MDSCs), which agent comprises SEK-1005, which is the cyclic peptide shown in Structural Formula (I), and/or FGF.

According to the present invention, use of SEK-1005 and/or FGF enables attraction of immunosuppressive cells such as Tregs and/or MDSCs to the site of interest. This results in formation of an immune-tolerant site, so that the need for immune suppression, which has been indispensable for allotransplantation of cells or a tissue, can be reduced or eliminated, and the patient does not need to regularly take an immunosuppressant after the transplantation. Moreover, the present invention can eliminate the risk of various infections and development of malignant tumors due to side effects of immunosuppressants, as well as the risk of damage to organs and occurrence of hypertension, hyperglycemia, and the like due to side effects of immunosuppressants. Moreover, the present invention is advantageous in that targeting of a particular molecule is not necessary since immune tolerance is induced for the entire transplanted tissue.

The agent of the present invention can also be a useful model for scientific analysis of the mechanism of immune tolerance.

EMBODIMENTS FOR CARRYING OUT THE INVENTION

The agent for forming an immune-tolerant site and the agent for attracting immunosuppressive cells of the present invention comprise SEK-1005 and/or FGF as an effective ingredient(s).

(SEK-1005)

SEK-1005 (structural formula: $C_{45}H_{70}N_8O_{13}$; name: Ser, 3-hydroxy-N-[2-hydroxy-1-oxo-2-tetrahydro-2-hydroxy-6-methyl-5-(2-methylpropyl)-2H-pyran-2-yl-propyl]-Leu-Pip (hexahydro-3-pyridazinecarbonyl)-N-hydroxy-Ala-N-methyl-Phe-Pip-rho-lactone) is the compound represented by the following structural formula, which is a cyclic peptide isolated from the culture liquid of an actinomycetes *Streptomyces nobilis*, or a dried product thereof.

(I)

The actinomycetes *Streptomyces nobilis*, which is used for obtaining SEK-1005, is available from public culture collections. For example, the strain deposited as JCM4274 in RIKEN, as ATCC 19252 in the US, or as CBS 198.65 in the Netherlands may be used. The method for obtaining SEK-1005 is not limited, and SEK-1005 may be obtained from a natural product such as the actinomycetes *Streptomyces nobilis*, or may be synthesized by a bioengineering method or an organic chemical method. For specific methods for obtaining SEK-1005 from the actinomycetes *Streptomyces nobilis*, reference may be made to WO 96/12732.

SEK-1005 may have one or more amino acid residues deleted, added, and/or substituted as long as SEK-1005 has the ability to induce immune tolerance. Such a compound is also included in the scope of the present invention. Further, SEK-1005 may be in the form of a salt, or may be a molecule having a modification(s), as long as the ability to induce immune tolerance is maintained. Such a compound is also included in the scope of the present invention. Examples of the modifications include addition of one or more of sugar chains, alkyl groups, amino groups, carboxyl groups, thiol groups, hydroxyl groups, sulfonyl groups, naturally occurring amino acids, non-naturally occurring amino acids, D-amino acids, and the like. SEK-1005 may be a hydrate or anhydrate. SEK-1005 can be dissolved in an appropriate solvent such as acetone, ethanol, propanol, chloroform, dichloromethane, dimethylformamide, dimethylsulfoxide, N-methyl-2-pyrrolidone, dimethyl ether, ethyl acetate, tetrahydrofuran, and polyethylene glycol.

Various reports have been made on the pharmacological actions of SEK-1005, use of SEK-1005 as a drug, and the like. For example, JP 2008-260692 A describes a pharmaceutical composition comprising SEK-1005, having an action to promote wound healing, action to suppress allergic and nonallergic inflammation, short-term immunosuppressive action, antimicrobial action, cytokine-inducing action, and the like. JP 10-259134 A describes a wound healing-promoting agent comprising SEK-1005. However, SEK-1005 has not been reported to have an immune-tolerant site forming action.

(FGF)

Although any FGF may be used as long as it is a protein belonging to the FGF family, bFGF (basic fibroblast growth factor), FGF-2 (fibroblast growth factor-2) or aFGF (acidic fibroblast growth factor) is preferred, and bFGF or FGF-2 is more preferred. The origin of the FGF is not limited, and the FGF is preferably derived from a human in cases where it is used for human. An example of human bFGF includes, but is not limited to, a protein comprising the amino acid sequence of UniProtKB/Swiss-Prot: P09038.3. The sequence of the FGF is preferably a full-length sequence, but may also be a partial sequence as long as the FGF has an immune-tolerant site forming action and an immunosuppressive-cell attracting action. The FGF may have a wild-type sequence, or may have the same sequence as a wild-type sequence except that one or several amino acids (e.g. one, two or three) are substituted, deleted, inserted, and/or added as long as the FGF has an immune-tolerant site forming action and an immunosuppressive-cell attracting action. The FGF may be produced by recombination, or may be chemically synthesized. The FGF may be a commercially available product.

The agent for forming an immune-tolerant site or the agent for attracting immunosuppressive cells of the present invention comprising as an effective component(s) SEK-1005 and/or FGF is capable of inducing immune tolerance in the site of its administration, by attraction of cells having immunosuppressive capacity such as Tregs or MDSCs.

(Agent for Forming an Immune-Tolerant Site)

The agent for forming an immune-tolerant site of the present invention comprising as an effective component(s) SEK-1005 and/or FGF can be especially preferably used as an agent for forming an immune-tolerant site for transplantation of pancreatic islets, pseudo-pancreatic islets prepared by artificial differentiation induction of stem cells, or the like. By application of the agent to the target site of transplantation (transplantation site), immunosuppressive cells are attracted to the transplantation site, so that rejection due to the transplantation becomes less likely to occur. Examples of the body tissue to which the agent for forming an immune-tolerant site is applied include, but are not limited to, subcutaneous tissues. The site where the agent for forming an immune-tolerant site is brought into contact with the subcutaneous tissue is not limited, and may be either on the surface of the subcutaneous tissue (at the border between the subcutaneous tissue and the dermis) or inside the subcutaneous tissue.

The agent for forming an immune-tolerant site may be composed of only SEK-1005 and/or FGF, or may also contain another/other component(s). Examples of the another/other component(s) include vehicles, disintegrators, binders, lubricants, surfactants, solubilizers, stabilizers, isotonic agents, suspending agents, emulsifiers, buffers, and solvents. In cases where the agent for forming an immune-tolerant site contains a component other than SEK-1005 and/or FGF, the content of SEK-1005 and/or FGF in the agent for forming an immune-tolerant site is not limited as long as SEK-1005 and/or FGF can produce its/their effect as an effective ingredient(s) of the agent for forming an immune-tolerant site.

The content of SEK-1005 and/or FGF in the agent for forming an immune-tolerant site is, for example, an amount that enables, on Day 7 to Day 14 after contacting said agent with a site in the body tissue, attraction of 1.3- to 3-times as many CD4$^+$Foxp3$^+$ cells to the site in the body tissue as compared to the case in which an agent containing neither SEK-1005 nor FGF is contacted with said site.

The content of SEK-1005 and/or FGF in the agent for forming an immune-tolerant site is an amount which enables attraction of CD4$^+$Foxp3$^+$ cells to the site in the body tissue such that the ratio of Foxp3$^+$ cells among CD4$^+$ cells becomes more than 10%, for example, not less than 15%, as analyzed using a flow cytometer on Day 7 to Day 14 after contacting SEK-1005 and/or FGF with the site in the body tissue. Although there is no upper limit of the ratio of Foxp3$^+$ cells among CD4$^+$ cells, the content of SEK-1005 and/or FGF in the agent for forming an immune-tolerant site is, for example, preferably an amount at which the ratio of Foxp3$^+$ cells among CD4$^+$ cells becomes not more than 50% or, for example, not more than 40%, as analyzed using a flow cytometer on Day 7 to Day 14 after contacting SEK-1005 and/or FGF with the site in the body tissue.

The method for bringing the agent for forming an immune-tolerant site into contact with the body tissue is not limited. Examples of the method include a method in which SEK-1005 and/or FGF which may contain another/other component(s) is/are embedded in the body tissue together with another/other material(s) such as a biocompatible material to allow slow release of SEK-1005 and/or FGF, and a method in which SEK-1005 and/or FGF which may contain another/other component(s) is/are regularly administered by injection or the like. From the viewpoint of easily controlling the time of contact between the agent for forming an immune-tolerant site and the body tissue, the method in which SEK-1005 and/or FGF is/are embedded in the body tissue together with a biocompatible material to allow slow release of SEK-1005 and/or FGF is preferred since a space for transplantation of a transplantation material can be secured after removal of the agent for forming an immune-tolerant site. The size (for example, area) of the body tissue with which the agent for forming an immune-tolerant site is brought into contact is not limited, and may be selected depending on the therapeutic method and/or the like.

The biocompatible material is not limited as long as the material allows release of the agent for forming an immune-tolerant site. Examples of the material constituting the biocompatible material include hydrogels, dried products of hydrogels, sponges, porous polymer blocks, porous bodies, porous sheets, and porous membranes.

Examples of the materials constituting the hydrogels include cellulose derivatives such as hydroxypropylmethylcellulose (HPMC), carboxymethylcellulose sodium (CMC-Na), and hydroxyethylcellulose (HEC); chemically cross-linked products of, and products prepared by radiation cross-linking or thermal cross-linking of, naturally-occurring polymers such as gelatin, alginic acid, albumin, collagen, starch, agarose, dextran, pullulan, pectin, hyaluronic acid, chitin, and chitosan; chemically cross-linked products of, and products prepared by radiation cross-linking or thermal cross-linking of, synthetic polymers such as polyvinyl alcohol, polyvinyl pyrrolidone, polyethylene glycol, poly-2-hydroxyethyl methacrylate, poly-2-hydroxyethyl acrylate, polyacrylamide, polyacrylic acid, and polymethacrylic acid; cross-linked products of copolymers composed of monomers constituting the above-described polymers; and polyion complex membranes of a polyanion and a polycation such as poly-L-lysine.

Examples of the sponges include those composed of the above-described porous polymers such as cellulose, agarose, chitosan, and collagen.

Examples of the materials constituting the porous bodies include organic and inorganic materials such as gelatin, silicone, and apatite.

The number of times in which the agent for forming an immune-tolerant site is brought into contact with the body tissue is not limited. The desired transplantation site (immune-tolerant site) may be formed by either one time of contact or a plurality of times of contact. The length of time for which the agent for forming an immune-tolerant site is brought into contact with the body tissue is not limited. The agent for forming an immune-tolerant site preferably has a constitution which, once embedded, allows continuous release of SEK-1005 and/or FGF from the biocompatible material or the like to the body tissue. The length of time for which SEK-1005 and/or FGF is/are continuously released from the biocompatible material or the like to the body tissue is preferably 1 day to 35 days, more preferably 2 days to 28 days, still more preferably 3 days to 21 days, especially preferably 4 days to 14 days.

The amount(s) of SEK-1005 and/or FGF is/are appropriately controlled depending on the size of the transplanted cell or transplanted tissue, and/or the like.

The immune-tolerant site formed using the agent for forming an immune-tolerant site of the present invention may be used for transplantation of various transplantation materials. The immune-tolerant site is especially preferred for transplantation of a transplantation material which can exert its function independently of the site of transplantation. Examples of such a transplantation material include tissues and cells which secrete a physiologically active substance such as a hormone, cytokine, neurotransmitter, or enzyme. Specific examples of the transplantation material include pancreatic islets, hepatocytes, adrenal, parathyroid, cells producing erythropoietin (e.g., stromal cells of uriniferous tubules), and cells producing growth hormone (e.g., GH secreting cells in the anterior pituitary gland). Other examples of the transplantation material include functional cells artificially produced by differentiation induction of somatic stem cells, induced pluripotent stem cells such as iPS cells, or embryonic stem cells (ES cells).

The transplantation material to be transplanted to the immune-tolerant site formed using the agent for forming an immune-tolerant site of the present invention may be a tissue (including an organ), cells, or the like which can survive at the transplantation site. The transplantation material may be derived from an organism, or may be artificially prepared. Since the agent for forming an immune-tolerant site of the present invention can form a site where the immune response is suppressed (immune-tolerant site), not only cells, tissues, and microtissues from the same species, but also cells, tissues, and microtissues from different species may be used as the transplantation material. In cases where cells, tissue, or microtissue from the same species is used, not only a tissue, cell, or microtissue from the same line of the same species, but also a tissue, cell, or microtissue from a different line of the same species may be used. Normally, tissues, cells, and microtissues from different species; and tissues, cells, and microtissues from different lines of the same species; are rapidly rejected when they are subcutaneously transplanted without any treatment. By performing their transplantation to the transplantation site in the present invention (immune-tolerant site), the immune response is suppressed, and hence the rejection can be avoided. Thus, the present invention can provide a desirable site of transplantation even in cases where such a cell or the like is used. The term "same species" means that the transplantation material is derived from the same species; the term "different species" means that the transplantation material is derived from a different species; the term "same line of the same species" means that "the transplantation material is derived from the same species and has the same genetic composition"; and the term "different line of the same species" means that "the transplantation material is derived from the same species but has a different genetic composition".

Transplantation of a tissue to an immune-tolerant site formed using the agent for forming an immune-tolerant site of the present invention is useful for treatment of various diseases. From the viewpoint of amelioration of symptoms and improvement of the quality of life, the effect of transplantation is especially large in cases of insulin-dependent diabetes mellitus, wherein secretion of insulin needs to be regularly controlled depending on changes in the blood glucose level, relative to other endocrine diseases. Thus, the agent for forming an immune-tolerant site of the present invention is especially useful in cases where it is used for formation of a site of transplantation of pancreatic islets for treatment of insulin-dependent diabetes mellitus.

Type I diabetes, which develops due to an autoimmune response, accounts for a large proportion of cases of such diabetes. However, the agent for forming an immune-tolerant site of the present invention is also useful in treatment of type II diabetes. That is, as type II diabetes progresses, the volume of pancreatic β cells decreases, and administration of insulin becomes necessary according to the current therapeutic method. Even in such cases, treatment of the disease is possible by transplantation of pancreatic islets to an immune-tolerant site formed using the agent for forming an immune-tolerant site of the present invention. From the viewpoint of the fact that type II diabetes occurs due to an increase in insulin resistance in the body rather than a decrease in insulin productivity in the pancreas, the transplantation may also be effectively carried out for the purpose of prevention of the disease before the disease progresses to a stage in which insulin administration is necessary.

Even in cases where a tissue derived from another individual is transplanted, the agent for forming an immune-tolerant site of the present invention allows formation of a transplantation site where an immunosuppressed state is maintained (immune-tolerant site). For example, in treatment of insulin-dependent diabetes mellitus by transplantation of pancreatic islets, a tissue donated by another individual is used. Therefore, the patient usually needs to regularly take an immunosuppressant after the transplantation. In cases where the agent for forming an immune-tolerant site of the present invention is used, the amount of the immunosuppressant to be taken can be reduced, or the need to take the immunosuppressant can be eliminated after the transplantation of pancreatic islets. Patients with insulin-dependent diabetes mellitus are mainly those with type I diabetes, which occurs due to an autoimmune response. Since the agent for forming an immune-tolerant site of the present invention enables formation of a transplantation site where the immune response is suppressed (immune-tolerant site), protection against the autoimmune response can also be expected at the site. Thus, the present method is useful also from the viewpoint of long-term maintenance of the function of transplanted pancreatic islets.

(Agent for Attracting Immunosuppressive Cells)

The agent for attracting immunosuppressive cells of the present invention comprising as an effective component(s) SEK-1005 and/or FGF can be especially preferably used in cases where pancreatic islets, pseudo-pancreatic islets prepared by artificial differentiation induction of stem cells, or the like are transplanted. By application of the agent for attracting immunosuppressive cells to the target site of transplantation (transplantation site), immunosuppressive cells are attracted to the transplantation site, so that rejection due to the transplantation becomes less likely to occur. Examples of the body tissue to which the agent for attracting immunosuppressive cells is applied include, but are not limited to, subcutaneous tissues. The area where the agent for attracting immunosuppressive cells is brought into contact with the subcutaneous tissue is not limited, and may be either on the surface of the subcutaneous tissue (at the border between the subcutaneous tissue and the dermis) or inside the subcutaneous tissue.

The agent for attracting immunosuppressive cells may be composed of only SEK-1005 and/or FGF, or may also contain another/other component(s). Examples of the another/other component(s) include vehicles, disintegrators, binders, lubricants, surfactants, solubilizers, stabilizers, isotonic agents, suspending agents, emulsifiers, buffers, and solvents. In cases where the agent for attracting immunosuppressive cells contains a component other than SEK-1005 and/or FGF, the content of SEK-1005 and/or FGF in the agent for attracting immunosuppressive cells is not limited as long as SEK-1005 and/or FGF can produce its/their effect as an effective ingredient(s) of the agent for attracting immunosuppressive cells.

The content of SEK-1005 and/or FGF in the agent for attracting immunosuppressive cells is, for example, an amount that enables, on Day 7 to Day 14 after contacting said agent with a site of the body tissue, attraction of 1.3- to 3-times as many $CD4^+Foxp3^+$ cells to the site of body tissue as compared to the case in which an agent containing neither SEK-1005 nor FGF is contacted with said site.

The content of SEK-1005 and/or FGF in the agent for attracting immunosuppressive cells is an amount which enables attraction of $CD4^+Foxp3^+$ cells to a site in a body tissue such that the ratio of $Foxp3^+$ cells among $CD4^+$ cells becomes more than 10%, for example, not less than 15%, as analyzed using a flow cytometer on Day 7 to Day 14 after contacting SEK-1005 and/or FGF with the site in the body tissue. Although there is no upper limit of the ratio of $Foxp3^+$ cells among $CD4^+$ cells, the content of SEK-1005 and/or FGF in the agent for attracting immunosuppressive cells is, for example, preferably an amount at which the ratio of $Foxp3^+$ cells among $CD4^+$ cells becomes not more than 50% or, for example, not more than 40%, as analyzed using a flow cytometer on Day 7 to Day 14 after contacting SEK-1005 and/or FGF with the site in the body tissue.

The method for bringing the agent for attracting immunosuppressive cells into contact with the body tissue is not limited. Examples of the method include a method in which SEK-1005 and/or FGF which may contain another/other component(s) is/are embedded in the body tissue together with another/other material(s) such as a biocompatible material to allow slow release of SEK-1005 and/or FGF, and a method in which SEK-1005 and/or FGF which may contain another/other component(s) is/are regularly administered by injection or the like. From the viewpoint of easily controlling the time of contact between the agent for attracting immunosuppressive cells and the body tissue, the method in which SEK-1005 and/or FGF is/are embedded in the body tissue together with a biocompatible material to allow slow release of SEK-1005 and/or FGF is preferred since a space for transplantation of a transplantation material can be secured after removal of the agent for attracting immunosuppressive cells. The size (for example, area) of the body tissue with which the agent for attracting immunosuppressive cells is brought into contact is not limited, and may be selected depending on the therapeutic method and/or the like.

The biocompatible material is not limited as long as the material allows release of the agent for attracting immunosuppressive cells. Examples of the material constituting the biocompatible material include hydrogels, dried products of hydrogels, sponges, porous polymer blocks, porous bodies, porous sheets, and porous membranes.

Examples of the materials constituting the hydrogels include cellulose derivatives such as hydroxypropylmethylcellulose (HPMC), carboxymethylcellulose sodium (CMC-Na), and hydroxyethylcellulose (HEC); chemically cross-linked products of, and products prepared by radiation cross-linking or thermal cross-linking of, naturally-occurring polymers such as gelatin, alginic acid, albumin, collagen, starch, agarose, dextran, pullulan, pectin, hyaluronic acid, chitin, and chitosan; chemically cross-linked products of, and products prepared by radiation cross-linking or thermal cross-linking of, synthetic polymers such as polyvinyl alcohol, polyvinyl pyrrolidone, polyethylene glycol, poly-2-hydroxyethyl methacrylate, poly-2-hydroxyethyl acrylate, polyacrylamide, polyacrylic acid, and polymethacrylic acid; cross-linked products of copolymers composed of monomers constituting the above-described polymers; and polyion complex membranes of a polyanion and a polycation such as poly-L-lysine.

Examples of the sponges include those composed of the above-described porous polymers such as cellulose, agarose, chitosan, and collagen Examples of the materials constituting the porous bodies include organic and inorganic materials such as gelatin, silicone, and apatite.

The number of times in which the agent for attracting immunosuppressive cells is brought into contact with the body tissue is not limited. The desired transplantation site (immune-tolerant site) may be formed by either one time of contact or multiple times of contact. The length of time for which the agent for attracting immunosuppressive cells is brought into contact with the body tissue is not limited. The agent for attracting immunosuppressive cells preferably has a constitution which, once embedded, allows continuous release of SEK-1005 and/or FGF from the biocompatible material or the like to the body tissue. The length of time for which SEK-1005 and/or FGF is/are continuously released from the biocompatible material or the like to the body tissue is preferably 1 day to 35 days, more preferably 2 days to 28 days, still more preferably 3 days to 21 days, especially preferably 4 days to 14 days.

The amount(s) of SEK-1005 and/or FGF is/are appropriately controlled depending on the size of the transplanted cell or transplanted tissue, and/or the like.

The immune-tolerant site formed using the agent for attracting immunosuppressive cells may be used for transplantation of various transplantation materials. The immune-tolerant site is especially preferred for transplantation of a transplantation material which can exert its function independently of the site of transplantation. Examples of such a transplantation material include tissues and cells which secrete a physiologically active substance such as a hormone, cytokine, neurotransmitter, or enzyme. Specific examples of the transplantation material include pancreatic islets, hepatocytes, adrenal, parathyroid, cells producing erythropoietin (e.g., stromal cells of uriniferous tubules), and cells producing growth hormone (e.g., GH secreting cells in the anterior pituitary gland). Other examples of the transplantation material include functional cells artificially produced by differentiation induction of somatic stem cells, induced pluripotent stem cells such as iPS cells, or embryonic stem cells (ES cells).

When transplantation is performed at the immune-tolerant site formed using the agent for attracting immunosuppressive cells of the present invention, it is preferable that the transplantation is performed after a substantial amount of immunosuppressive cells sufficient for establishing immune tolerance at the site are attracted to the site. For example, it is preferable that the transplantation is performed seven days, more preferably ten days after the agent for attracting immunosuppressive cells is brought into contact with a site of a body tissue where transplantation material is to be introduced.

The transplantation material to be transplanted to the immune-tolerant site formed using the agent for attracting immunosuppressive cells of the present invention may be a tissue (including an organ), cells, or the like which can survive at the transplantation site. The transplantation material may be derived from an organism, or may be artificially prepared. Since the agent for attracting immunosuppressive cells of the present invention can form a site where the immune response is suppressed (immune-tolerant site), not only cells, tissues, and microtissues from the same species, but also cells, tissues, and microtissues from different species may be used as the transplantation material. In cases where a cell or a tissue from the same species is used, not only a tissue, cell, or microtissue from the same line of the same species, but also a tissue, cell, or microtissue from a different line of the same species may be used. Normally, tissues, cells, and microtissues from different species; and tissues, cells, and microtissues from different lines of the same species; are rapidly rejected when they are subcutaneously transplanted without any treatment. By performing their transplantation to the transplantation site in the present invention (immune-tolerant site), the immune response is suppressed, and hence the rejection can be avoided. Thus, the present invention can provide a desirable site of transplantation even in cases where such a cell or the like is used. The term "same species" means that the transplantation material is derived from the same species; the term "different species" means that the transplantation material is derived from a different species; the term "same line of the same species" means that "the transplantation material is derived from the same species and has the same genetic composition"; and the term "different line of the same species" means that "the transplantation material is derived from the same species but has a different genetic composition".

Transplantation of a tissue to an immune-tolerant site formed using the agent for attracting immunosuppressive cells of the present invention is useful for treatment of various diseases. From the viewpoint of amelioration of symptoms and improvement of the quality of life, the effect of transplantation is especially large in cases of insulin-dependent diabetes mellitus, wherein secretion of insulin needs to be regularly controlled depending on changes in the blood glucose level, relative to other endocrine diseases. Thus, the agent for attracting immunosuppressive cells of the present invention is especially useful in cases where it is used for formation of a site of transplantation of pancreatic islets for treatment of insulin-dependent diabetes mellitus.

Type I diabetes, which develops due to an autoimmune response, accounts for a large proportion of cases of such diabetes. However, the agent for attracting immunosuppressive cells of the present invention is also useful in treatment of type II diabetes. That is, as type II diabetes progresses, the volume of pancreatic β cells decreases, and administration of insulin becomes necessary according to the current therapeutic method. Even in such cases, treatment of the disease is possible by transplantation of pancreatic islets to an immune-tolerant site formed using the agent for attracting immunosuppressive cells of the present invention. From the viewpoint of the fact that type II diabetes occurs due to an increase in insulin resistance in the body rather than a decrease in insulin productivity in the pancreas, the transplantation may also be effectively carried out for the purpose of prevention of the disease before the disease progresses to a stage in which insulin administration is necessary.

Even in cases where a tissue derived from another individual is transplanted, the agent for attracting immunosuppressive cells of the present invention allows formation of a transplantation site where an immunosuppressed state is maintained (immune-tolerant site). For example, in treatment of insulin-dependent diabetes mellitus by transplantation of pancreatic islets, a tissue donated by another individual is used. Therefore, the patient usually needs to regularly take an immunosuppressant after the transplantation. In cases where the agent for attracting immunosuppressive cells of the present invention is used, the amount of the immunosuppressant to be taken can be reduced, or the need to take the immunosuppressant can be eliminated after the transplantation of pancreatic islets. Patients with insulin-dependent diabetes mellitus are mainly those with type I diabetes, which occurs due to an autoimmune response. Since the agent for attracting immunosuppressive cells enables formation of a transplantation site where the immune response is suppressed (immune-tolerant site), protection against the autoimmune response can also be expected at the site. Thus, the present method is useful also from the viewpoint of long-term maintenance of the function of transplanted pancreatic islets. The agent for attracting immunosuppressive cells of the present invention has an advantageous effect that the functions and effects of the transplanted material such as pancreatic islets are maintained and thus the treatment effect with the transplanted material is prolonged since immune tolerance is maintained for a long period of time, e.g., more than 100 days at the site where the agent has been introduced.

Patients as referred to herein and to whom the uses, methods and agents of the invention may be applied are preferably mammalian animals, particularly humans. A subject as referred to herein may similarly be a mammalian animal, particularly a human.

As described herein, the invention extends to the agent as described herein for use in treating or preventing rejection of a transplant in a patient. Preferably the transplant is tissues or cells, preferably pancreatic islets. In such a use rejection may be treated or prevented by use of the agent to prepare or treat the site of transplantation, e.g. by administration of the agent to the site of transplantation before, during or after the transplantation (as described herein). Thus the agent may be used to prepare a site for transplantation. The invention also extends to the agent as described herein for use in treating a patient, wherein said treatment comprises transplantation, preferably transplantation of pancreatic islets. In such a use said treatment may comprise use of the agent to prepare or treat the site of transplantation, e.g. by administration of the agent to the site of transplantation before, during or after the transplantation (as described herein). Further encompassed is the agent as described herein for use in treating or preventing diabetes in a patient, wherein said treatment comprises transplantation, preferably transplantation of pancreatic islets. In such a use said treatment or prevention may comprise use of the agent to prepare or treat the site of transplantation, e.g. by administration of the agent to the site of transplantation before, during or after the transplantation (as described herein). In the above uses the agent forms an immune-tolerant site for transplant or attracts immunosuppressive cells to the transplant site. Also provided is a method of forming an immune-tolerant site in a body tissue in a subject, or attracting immunosuppressive cells to a site in a body tissue in a subject, comprising administering an agent as described herein to said site. Such uses and methods are preferably performed as described herein, e.g. in terms of the amount of the agent to be used.

EXAMPLES

The present invention is described below more concretely by referring to Examples. However, the present invention is not limited to the following embodiments.

Example 1

Analysis of Exudate and Immune Cells in a Tissue Portion in Which SEK-1005-Containing Agarose Rod was Embedded In a polystyrene tube with an inner diameter of 4 mm, 4.5% agarose solution was poured, and the tube was then left to stand at normal temperature to allow gelation of the agarose solution. The resulting agarose gel rod was removed from the polystyrene tube, and cut into a piece having a length of 25 mm. Subsequently, the agarose gel rod was stored in a freezer at −30° C. overnight to allow freezing of water. By freeze-drying the frozen agarose rod, a porous dry agarose rod was prepared. To the dry agarose rod, 50 µl of a solution of 2 mg/ml SEK-1005 in ethanol was added dropwise to include the SEK-1005 solution in the dry agarose rod. Ethanol was then evaporated by air drying.

On the day when the agarose rod was to be embedded, streptozotocin (STZ) (60 mg/kg body weight) was administered to ACI rats to induce diabetes. To each of the left side and the right side of the back of each ACI rat, the agarose rod having a length of 25 mm and a diameter of 4 mm containing 100 µg of SEK-1005 was embedded. On Day 10 after the embedding, the agarose rod was removed. In the vicinity of each place where the agarose rod had been embedded, formation of connective tissue containing a number of blood vessels was found. This tissue was minced with scissors, and then homogenized, followed by collecting cells from the tissue. The cells were subjected to purification by Percoll density gradient centrifugation to obtain immune cells, and the obtained immune cells were analyzed using a flow cytometer.

Figure 1:
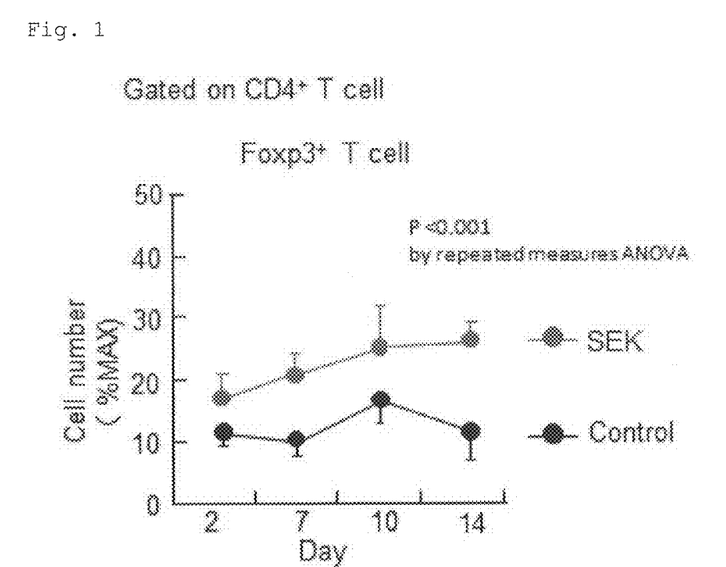
FIG. 1 is a diagram showing the results of flow cytometry of cells collected from rat tissues in which an SEK-1005-containing agarose rod or an SEK-1005-free agarose rod was embedded under the skin. The ordinate represents the ratio of CD4$^+$Foxp3$^+$ cells among CD4$^+$ cells, which is an index of regulatory T cells.

FIG. 1 shows the result of the analysis of $CD4^+$, and $Foxp3^+$ which is a marker for regulatory T cells, using the flow cytometer. The ratio of $Foxp3^+$ cells among $CD4^+$ cells was 18.3% on Day 2, 20.8% on Day 7, 23.3% on Day 10, and 27.3% on Day 14 after the SEK-1005-containing agarose rod was embedded under the skin. Since this ratio is about 10% in normal subcutaneous tissues, it was found that the ratio of regulatory T cells ($CD4^+Foxp3^+$ cells) increased about 2- to 3-fold due to the action of SEK-1005.

Figure 2:
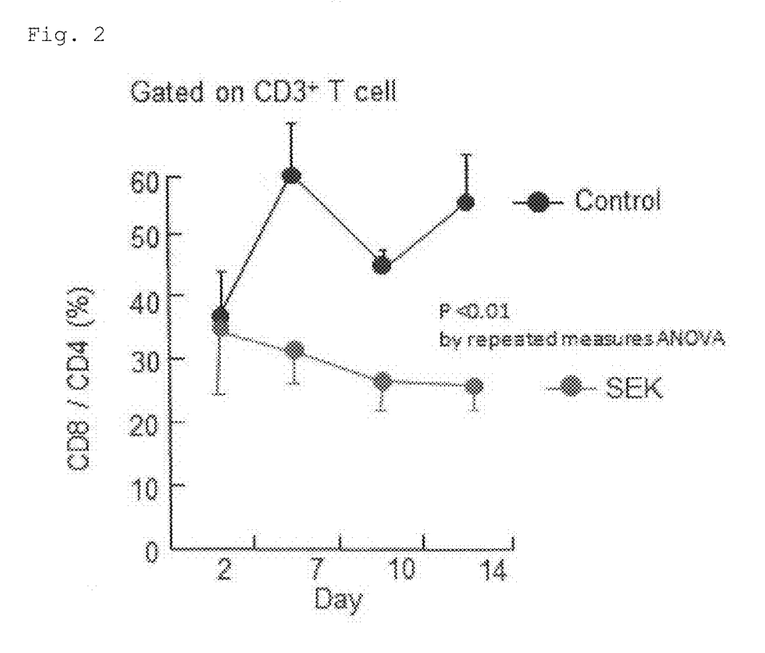
FIG. 2 is a diagram showing the results of flow cytometry of cells collected from rat tissues in which an SEK-1005-containing agarose rod or an SEK-1005-free agarose rod was embedded under the skin. The ordinate represents the ratio of CD8$^+$ cells to CD4$^+$ cells among CD3$^+$ cells, which is an index of cytotoxic T cells.

On the other hand, as shown in FIG. 2, the ratio of cytotoxic T cells ($CD8^+$ T cells) to $CD4^+$ cells among $CD3^+$ cells was 36.1% on Day 2, 33.7% on Day 7, 25.5% on Day 10, and 23.9% on Day 14 after the SEK-1005-containing agarose rod was embedded under the skin. In normal subcutaneous tissues, the ratio is about 30%, and, when a foreign substance is embedded, the ratio increases to not less than 50% in most cases. The action of SEK-1005 suppressed such an increase.

The TGF-β1 concentration in the exudate was measured. The TGF-β1 concentration was 0.7±0.1 ng/ml until Day 7 after the SEK-1005-containing agarose rod was embedded. However, the TGF-β1 concentration gradually increased thereafter, and reached 2.0±1.0 ng/ml on Day 10 after the embedding. This was about 3 times the concentration in a treated group in which an SEK-1005-free agarose rod was embedded. The concentration gradually decreased thereafter.

Comparative Example 1

Analysis of Immune Cells at Site Where SEK-1005-Free Agarose Rod was Embedded

In a polystyrene tube with an inner diameter of 4 mm, 4.5% agarose solution was poured, and the tube was then left to stand at normal temperature to allow gelation of the agarose solution. The resulting agarose gel rod was removed from the polystyrene tube, and cut into a piece having a length of 25 mm. Subsequently, the agarose gel rod was stored in a freezer at −30° C. overnight to allow freezing of water. By freeze-drying the frozen agarose rod, a porous dry agarose rod was prepared.

On the day when the agarose rod was to be embedded, streptozotocin (STZ) (60 mg/kg body weight) was administered to ACI rats to induce diabetes. To each of the left side and the right side of the back of each ACI rat, the agarose rod having a length of 25 mm and a diameter of 4 mm containing no SEK-1005 was embedded. On Day 10 after the embedding, the agarose rod was pulled out. The tissue in the vicinity of each place where the agarose rod had been embedded was minced with scissors, and then homogenized, followed by collecting cells from the tissue. The cells were subjected to purification by Percoll density gradient centrifugation to obtain immune cells, and the obtained immune cells were analyzed using a flow cytometer.

FIG. 1 shows the result of the analysis of CD4$^+$, and Foxp3 which is a marker for regulatory T cells. The ratio of CD4$^+$Foxp3$^+$ cells among CD4$^+$ cells, which is an index of regulatory T cells, was 11.3% on Day 2, 10.5% on Day 7, 17.1% on Day 10, and 11.3% on Day 14 after the SEK-1005-free agarose rod was embedded under the skin. Since this ratio is about 10% in normal subcutaneous tissues, it was found that the ratio of regulatory T cells slightly increased due to the action of the SEK-1005-free agarose rod. However, no remarkable increase in the ratio was found.

As shown in FIG. 2, when the SEK-1005-free agarose rod was embedded under the skin, the ratio of cytotoxic T cells to CD4$^+$ cells increased to not less than 40%. On the other hand, the ratio of cytotoxic T cells (CD8$^+$) to CD4$^+$ cells among CD3$^+$ cells was 36.1% on Day 2, 33.7% on Day 7, 25.5% on Day 10, and 23.9% on Day 14 when the SEK-1005-containing agarose rod was embedded under the skin. Thus, the increase in cytotoxic T cells was suppressed by the SEK-1005-containing agarose rod.

Example 2

Evaluation of Immunosuppressive Function of CD4$^+$CD25$^+$ Cells Which Accumulated at Site Where SEK-1005-Containing Agarose Rod was Embedded On Day 10 after embedding of the SEK-1005-containing agarose rod by the same operation as in Example 1, the tissue in the vicinity of the place where the rod was embedded was collected, and then homogenized, followed by collecting cells from the tissue. The cells were subjected to purification by Percoll density gradient centrifugation to obtain immune cells, and CD4$^+$CD25$^+$ cells (a fraction containing a large number of tissue-infiltrating regulatory T cells) were collected using MACS magnetic beads.

CD8$^+$ T cells were separately prepared from ACI rats, and the cells were then stained with a fluorescent dye, carboxyfluorescein succinimidyl ester (CFSE). On a 96-well plate, 2.5×10$^4$ CD8$^+$ T cells and 5×10$^4$ antigen-presenting cells were plated in each well, and the cell growth was quantitatively evaluated using a flow cytometer on Day 4.5 after the plating. The wells were divided into three groups. In Group 1, 1 µg/mL anti-CD3 antibody was added to stimulate the growth. In Group 2, 1 µg/mL anti-CD3 antibody as well as 2.5×10$^4$ CD4$^+$CD25$^+$ cells were added. In Group 3, no anti-CD3 antibody was added.

Figure 3:
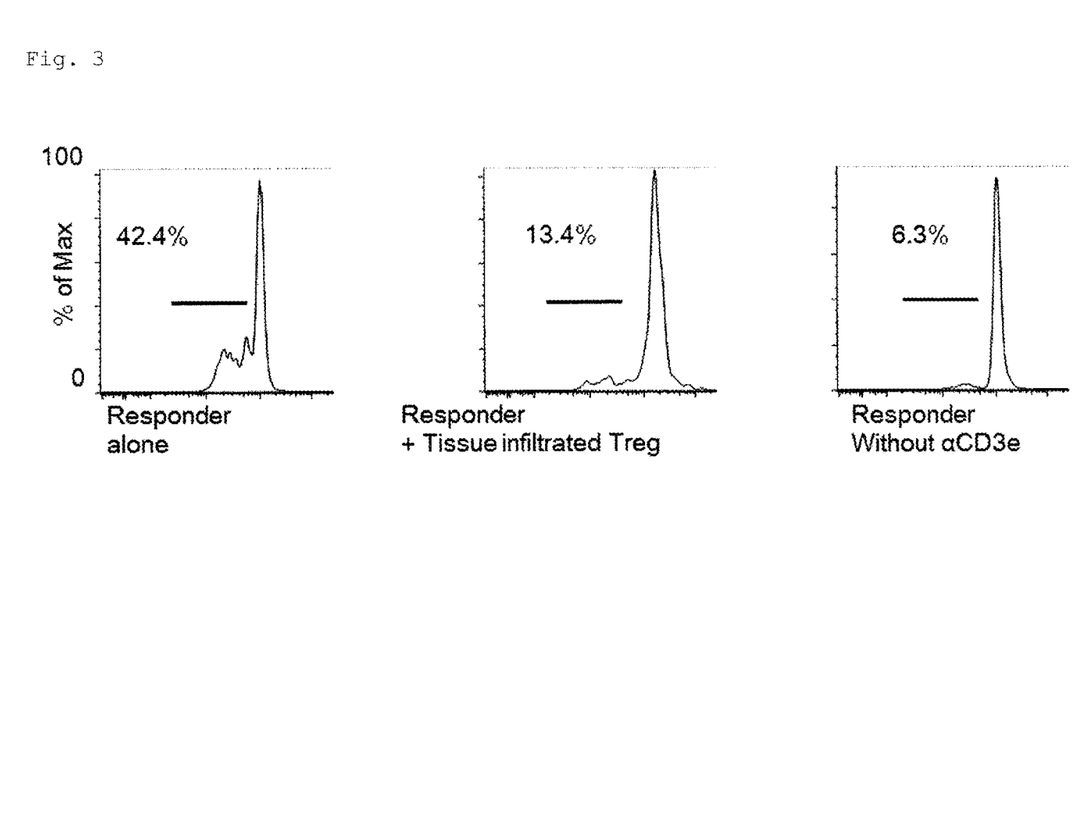
FIG. 3 is a diagram showing the results of a Treg suppression assay. The left panel (Group 1) shows the result obtained for a case where growth stimulation was carried out by addition of 1 μg/mL anti-CD3 antibody; the middle panel (Group 2) shows the result obtained for a case where 1 μg/mL anti-CD3 antibody as well as 2.5×10$^4$ CD4$^+$CD25$^+$ cells including a large number of regulatory T cells were added; and the right panel (Group 3) shows the result obtained for a case where no anti-CD3 antibody was added.

FIG. 3 shows the representative flow cytograms which were obtained. One round of cell division of T cells stained with a fluorescent dye results in a decrease in the fluorescence intensity to half. Another division results in a decrease in the fluorescent intensity to one fourth of the original intensity. As can be seen in the flow cytogram shown in the right panel of FIG. 3 (Group 3), cells exhibiting decreased fluorescence intensity accounted for 6.3% of the total number of cells. These were thought to be cells that naturally divided during the culture. On the other hand, as can be seen in the flow cytogram shown in the left panel of FIG. 3 (Group 1), which shows the result of analysis of the cells to which the anti-CD3 antibody was added, cells exhibiting decreased fluorescence intensity accounted for as much as 42.4% of the total number of cells. Thus, it can be seen that cell division occurred in a large number of cells during the culture period of 4.5 days. The middle panel of FIG. 3 shows a flow cytogram obtained by adding the anti-CD3 antibody as well as 2.5×10$^4$ CD4$^+$CD25$^+$ cells (a fraction containing a large number of tissue-infiltrating regulatory T cells) collected from the tissue in the vicinity of the SEK-1005-containing agarose rod, to a well (Group 2). The ratio of cells exhibiting decreased fluorescence intensity due to cell division was 13.4%. Thus, a remarkable decrease in the ratio was found as compared to the ratio in Group 1, 42.4%. That is, the CD4$^+$CD25$^+$ cells collected from the tissue in the vicinity of the SEK-1005-containing agarose rod were found to have the ability to suppress the growth of T cells.

Example 3

Gene Expression Analysis of Tissue in Vicinity of Embedded SEK-1005-Containing Agarose Rod On Day 7 after embedding of the SEK-1005-containing agarose rod by the same operation as in Example 1, the tissue in the vicinity of the place where the rod was embedded was collected. The collected tissue was immediately impregnated with RNA later solution (Life Technologies) to inhibit RNA degradation. RNA in the tissue was extracted by the column method. The extracted RNA was amplified by the Express kit method (Affymetrix) and biotin-labeled, followed by hybridization with a Rat Genome 230 2.0 array (Affymetrix). Signals were read by a Hewlett-Packard GeneArray Scanner G2500A. By such a process, gene expression analysis was carried out for three tissue samples obtained from the vicinities of SEK-1005-containing agarose rods and three tissue samples obtained from the vicinities of control SEK-1005-free agarose rods. The obtained fluorescence intensities were standardized and normalized, and then subjected to statistical analysis. The standardized and normalized gene expression level was statistically compared between the SEK-1005-containing agarose rod group and the control SEK-1005-free agarose rod group. Genes showing increased expression in the SEK-1005-containing agarose rod group were plotted such that their values along the X-axis became positive. Log 2 conversion was carried out in terms of the X-axis. Significance of difference between the two groups was plotted along the Y-axis after –Log 10 conversion of the P value (Volcano plot, upper left panel of FIG. 4).

Figure 4:
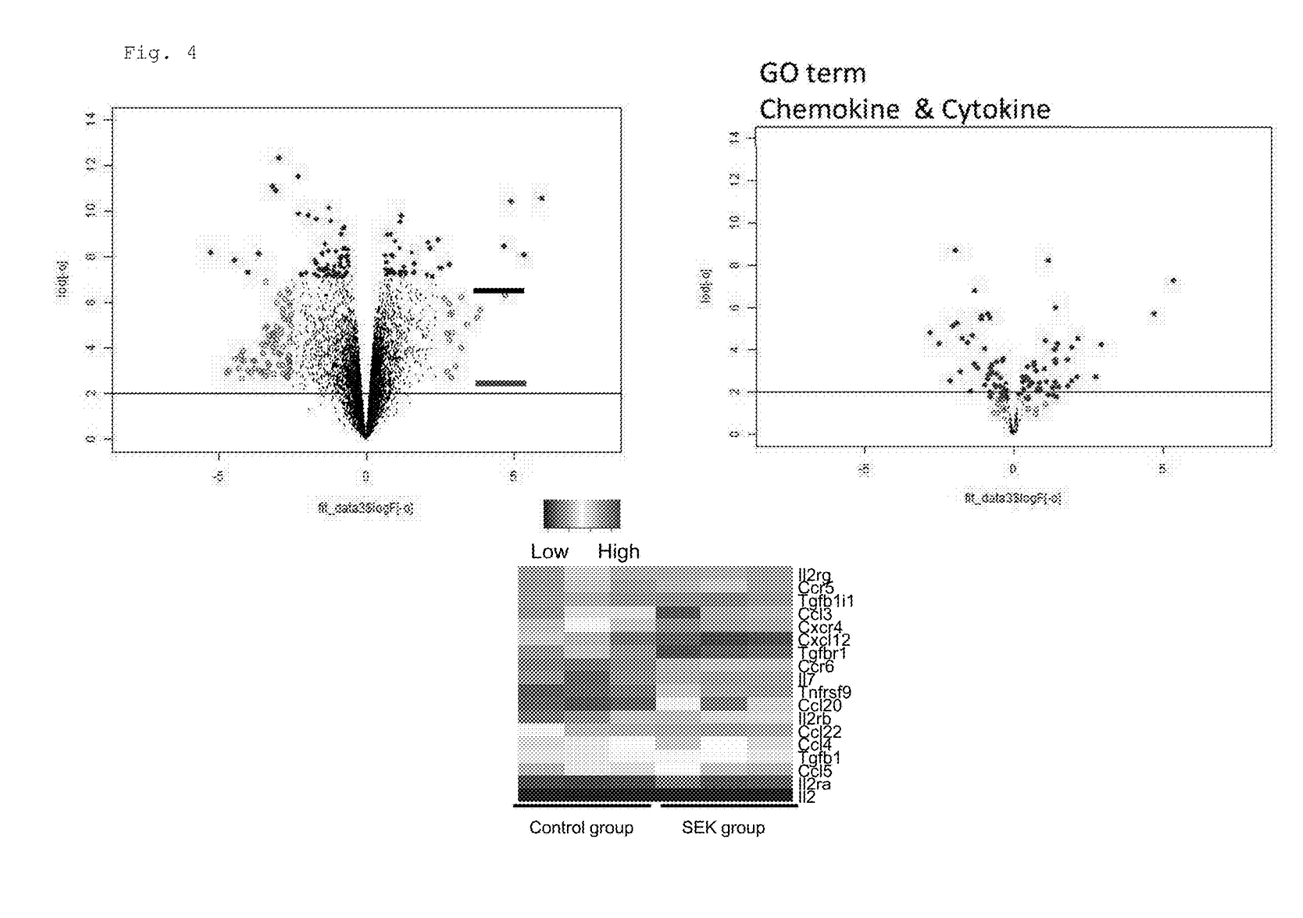
FIG. 4 is a diagram showing the results of analysis of gene expression in the surrounding tissue of the SEK-1005-containing agarose rod. The upper left panel is a volcano plot showing the whole gene expression. The upper right panel is a volcano plot showing expression of chemokine/cytokine-associated genes. The lower panel is a heat map showing expression of chemokine/cytokine-associated genes related to regulatory T cells.

As a result of the comprehensive gene expression analysis, the SEK-1005-containing agarose rod group was found to exhibit a significant increase in expression of genes associated with migration/induction of regulatory T cells among chemokine/cytokine-associated genes, and a significant decrease in expression of genes which are not associated with migration/induction of regulatory T cells among chemokine/cytokine-associated genes. Expression of the chemokine/cytokine-associated genes is shown as a volcano plot in the upper right panel of FIG. 4. In addition, expression of chemokine/cytokine-associated genes related to regulatory T cells is shown as a heat map (FIG. 4, lower panel). From these results, it was considered that the SEK-1005-containing agarose rod increases expression of chemokine/cytokine-associated genes related to regulatory T cells, leading to an increase in regulatory T cells and suppression of cytotoxic T cells (CD8) in the vicinity of the SEK-1005-containing agarose rod, thereby providing an environment in which immune tolerance to the transplanted organ is achieved.

Example 4

Analysis of Immune Cells at Site Where bFGF-Containing Agarose Rod was Embedded

In a polystyrene tube with an inner diameter of 4 mm, 4.5 agarose solution was poured, and the tube was then left to stand at normal temperature to allow gelation of the agarose solution. The resulting agarose gel rod was removed from the polystyrene tube, and cut into a piece having a length of 25 mm. Subsequently, the agarose gel rod was stored in a freezer at −30° C. overnight to allow freezing of water. By freeze-drying the frozen agarose rod, a porous dry agarose rod was prepared. To the dry agarose rod, 100 μl of 500 μg/ml bFGF solution (FIBLAST Spray 500, Kaken Pharmaceutical Co., Ltd.) was added dropwise to include the bFGF solution in the dry agarose rod.

On the day when the agarose rod was to be embedded, streptozotocin (STZ) (60 mg/kg body weight) was administered to ACI rats to induce diabetes. To each of the left side and the right side of the back of each ACI rat, the agarose rod having a length of 25 mm and a diameter of 4 mm containing 50 μg of bFGF was embedded. On Day 7 after the embedding, the agarose rod was pulled out. In the vicinity of each place where the agarose rod had been embedded, formation of connective tissue containing a number of blood vessels was found. This tissue was collected, and then minced with scissors, followed by homogenization. The cells were then subjected to purification by Percoll density gradient centrifugation to obtain immune cells, and the obtained immune cells were analyzed using a flow cytometer.

Figure 5:
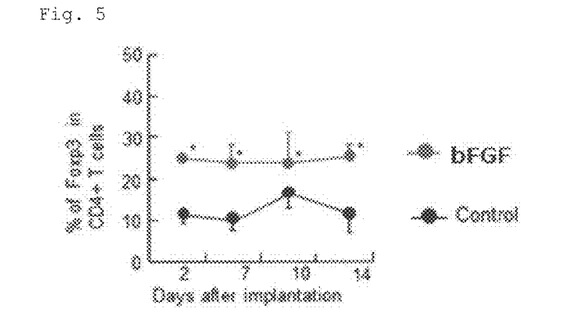
FIG. 5 is a diagram showing the results of flow cytometry of cells collected from rat tissues in which a bFGF-containing agarose rod or a bFGF-free agarose rod was embedded under the skin. The ordinate represents the ratio of CD4$^+$Foxp3$^+$ cells among CD4$^+$ cells, which is an index of regulatory T cells.

FIG. 5 shows the result of the analysis of $CD4^+$, and Foxp3 which is a marker for regulatory T cells. The ratio of $Foxp3^+$ cells among $CD4^+$ cells was 25.4% on Day 2, 24.4% on Day 7, 24.4% on Day 10, and 26.4% on Day 14 after the bFGF-containing agarose rod was embedded under the skin. Since this ratio is about 10% in normal subcutaneous tissues and the subcutaneous tissues of bFGF-free agarose rod-embedded rats, it was found that the ratio of regulatory T cells increased about 2- to 3-fold due to the action of bFGF.

Figure 6:
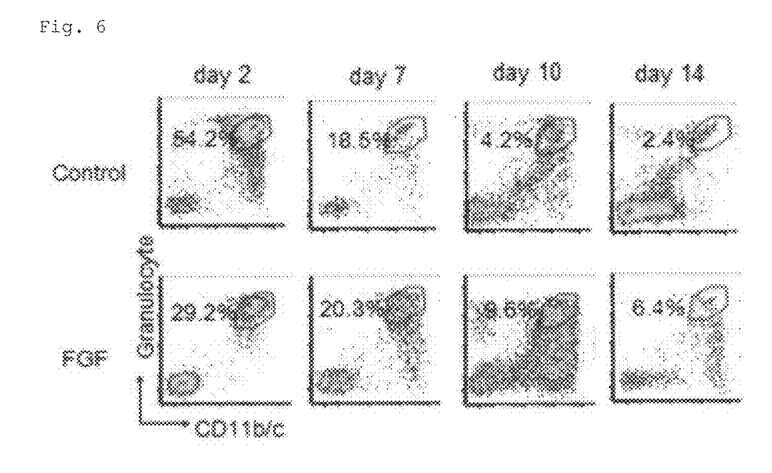
FIG. 6 is a diagram showing the results of flow cytometry of cells collected from rat tissues in which a bFGF-containing agarose rod or a bFGF-free agarose rod was embedded under the skin, which flow cytometry was carried out for CD11b/c and granulocytes.

In the group in which the agarose rod-bFGF was embedded, an increase in a granulocyte marker was found. Thus, it was found that myeloid-derived suppressor cells (MDSCs) were also induced (FIG. 6).

Example 5

Gene Expression Analysis of Tissue in Vicinity of Embedded bFGF-Containing Agarose Rod On Day 7 after embedding of the bFGF-containing agarose rod by the same operation as in Example 4, the tissue in the vicinity of the place where the rod was embedded was collected. The collected tissue was immediately impregnated with RNA later solution (Life Technologies) to inhibit RNA degradation. RNA in the tissue was extracted by the column method. The extracted RNA was amplified by the Express kit method (Affymetrix) and biotin-labeled, followed by hybridization with a Rat Genome 230 2.0 array (Affymetrix). Signals were read by a Hewlett-Packard Gene-Array Scanner G2500A. By such a process, gene expression analysis was carried out for three tissue samples obtained from the vicinities of bFGF-containing agarose rods and three tissue samples obtained from the vicinities of control bFGF-free agarose rods. The obtained fluorescence intensities were standardized and normalized, and then subjected to statistical analysis. The standardized and normalized gene expression level was statistically compared between the bFGF-containing agarose rod group and the control bFGF-free agarose rod group. Genes showing increased expression in the bFGF-containing agarose rod group were plotted such that their values along the X-axis became positive. Log 2 conversion was carried out in terms of the X-axis. Significance of difference between the two groups was plotted along the Y-axis after −Log 10 conversion of the P value (Volcano plot). As a result of the comprehensive gene expression analysis, the agarose rod-bFGF group was found to exhibit a significant increase in expression of genes associated with migration/induction of regulatory T cells among chemokine/cytokine-associated genes, and a significant decrease in expression of genes which are not associated with migration/induction of regulatory T cells among chemokine/cytokine-associated genes. Expression of the chemokine/cytokine-associated genes is shown as a volcano plot in FIG. 7(a). In addition, expression of chemokine/cytokine-associated genes related to regulatory T cells is shown as a heat map in FIG. 7(b).

Figure 7:
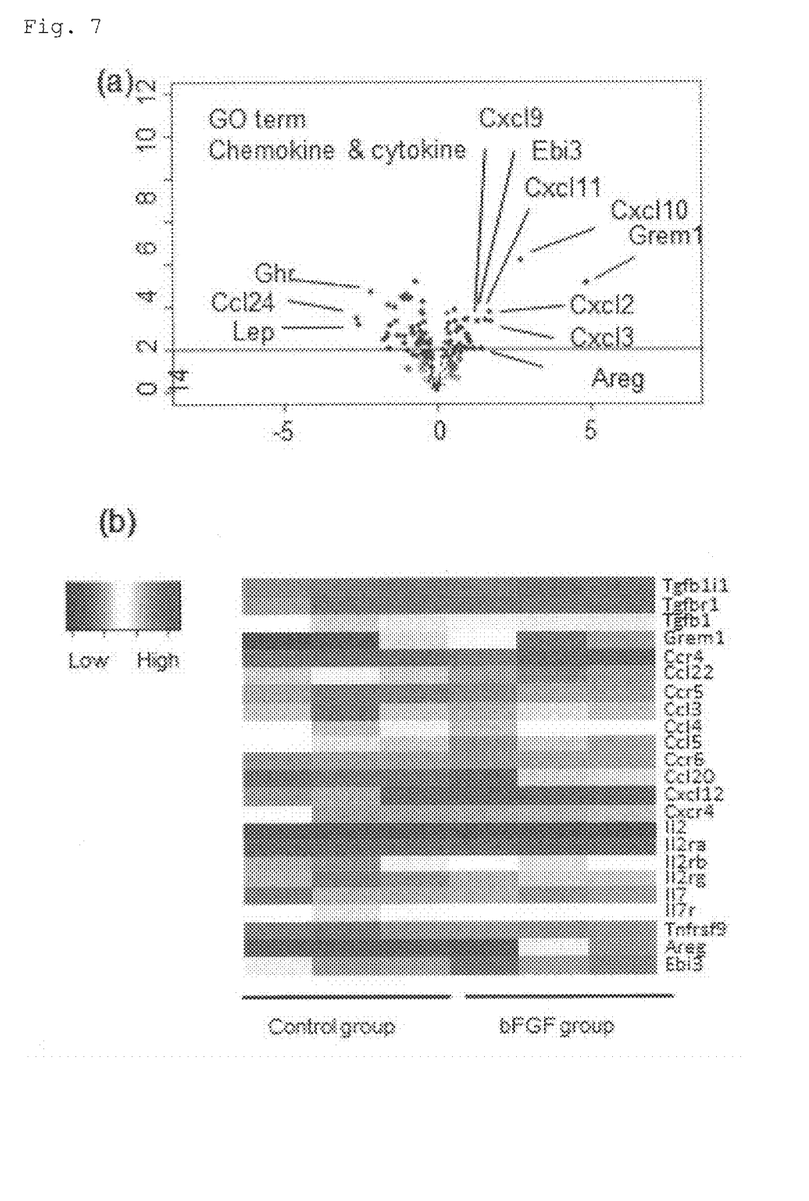
FIG. 7 is a diagram showing the results of analysis of gene expression in the surrounding tissue of the bFGF-containing agarose rod. Panel (a) is a volcano plot showing expression of chemokine/cytokine-associated genes. Panel (b) is a heat map showing expression of chemokine/cytokine-associated genes related to regulatory T cells.

From these results, it was thought that the bFGF-containing agarose rod increases expression of chemokine/cytokine-associated genes related to regulatory T cells, leading to an increase in regulatory T cells and suppression of cytotoxic T cells (CD8) in the vicinity of the bFGF-containing agarose rod, thereby providing an environment in which immune tolerance to the transplanted organ is achieved.

Example 6

Evaluation of Blood Glucose Level after Transplantation of Pancreatic Islets into the Site Where the SEK-1005-Containing Agarose rod Was Embedded On the day when the SEK-1005-containing agarose rod was to be embedded, streptozotocin (STZ) (60 mg/kg body weight) was administered to ACI rats to induce diabetes. Under the skin of each of the left side and the right side of the back of each ACI rat, the agarose rod prepared in the same way as Example 1 was embedded. On Day 2 or Day 10 after the embedding, the agarose rod was removed, and 1,500 pieces of pancreatic islets separated from the pancreases of F344 rats were transplanted to each of the two dorsal subcutaneous cavities formed. After the transplantation, the blood glucose levels of the rats were measured. As a result, it was found that the blood glucose levels were normalized in ACI rats in which the SEK-1005-containing agarose rod was embedded for ten days followed by removal of the rod and transplantation of pancreatic islets, whereas the blood glucose levels remained high (>400 mg/dL) in ACI rats in which the SEK-1005-containing agarose rod was embedded for two days followed by removal of the rod and transplantation of pancreatic islets. These results suggest that it takes a certain period of time after embedding the SEK-1005-containing agarose rod for formation of immune-tolerant site suitable for transplantation. When SEK-1005-free agarose rod was embedded in the STZ-administered rats for 10 days and after removal of the agarose-rod, pancreatic islets were transplanted to the embedded site, the blood glucose levels of the diabetic rats were not decreased.

While the invention has been described in detail with reference to preferred embodiments thereof, it will be apparent to one skilled in the art that various changes can be made, and equivalents employed, without departing from the scope of the invention. Each of the aforementioned documents as well as JP2015-082847 is incorporated by reference herein in its entirety.

What is claimed is:

1. A method for forming an immune-tolerant site in a body tissue comprising contacting an agent comprising SEK-1005 (Ser,3-hydroxy-N-[2-hydroxy-1-oxo-2-tetrahydro-2-hydroxy-6-methyl-5-(2-methylpropyl)-2H-pyran-2-yl-propyl]-Leu-Pip(hexahydro-3-pyridazinecarbonyl)-N-hydroxy-Ala-N-methyl-Phe-Pip-rho-lactone) with a site in the body tissue, wherein said agent comprises SEK-1005 in an amount which attracts immunosuppressive cells to the site in the body tissue to form the immune-tolerant site, wherein the body tissue is a subcutaneous tissue and wherein the immunosuppressive cells are regulatory T-cells or myeloid-derived suppressor cells.

2. The method according to claim 1, wherein said agent further comprises a biocompatible material.

3. The method according to claim 2, wherein said biocompatible material is a hydrogel.

4. The method according to claim 1, wherein said agent comprises SEK-1005 in an amount that, on Day 7 to Day 14 after contacting said agent with the site of the body tissue, attracts 1.3 to 3 times as many $CD4^+Foxp3^+$ cells to the site in the body tissue as compared to a control site where a control agent containing no SEK-1005 is contacted to the site under the same conditions.

5. A method for attracting immunosuppressive cells to a site in a body tissue comprising:
   contacting an agent comprising SEK-1005 with the site in the body tissue,
   wherein said agent comprises SEK-1005 in an amount which attracts the immunosuppressive cells to the site,
   wherein the body tissue is a subcutaneous tissue, and
   wherein the immunosuppressive cells are regulatory T-cells or myeloid-derived suppressor cells.

6. The method according to claim 5, wherein said agent further comprises a biocompatible material.

7. The method according to claim 6, wherein said biocompatible material is a hydrogel.

8. The method according to claim 5, wherein said agent comprises SEK-1005 in an amount that, on Day 7 to Day 14 after contacting said agent with the site in the body tissue, attracts 1.3 to 3 times as many CD4+Foxp3+ cells to the site in the body tissue as compared to a control site-where a control agent containing no SEK-1005 is contacted to the site under the same conditions.

* * * * *